(12) United States Patent
Okubo et al.

(10) Patent No.: US 8,212,028 B2
(45) Date of Patent: Jul. 3, 2012

(54) METHOD FOR PRODUCING ε-CAPROLACTAM AND METHOD FOR PRODUCING PENTASIL TYPE ZEOLITE

(75) Inventors: Tatsuya Okubo, Tokyo (JP); Yuki Suzuki, Osaka (JP); Tsuyoshi Matsushita, Ehime (JP); Tatsuya Suzuki, Ehime (JP)

(73) Assignees: Sumitomo Chemical Company, Limited, Tokyo (JP); The University of Tokyo, Tokyo (JP)

( * ) Notice: Subject to any disclaimer, the term of this patent is extended or adjusted under 35 U.S.C. 154(b) by 357 days.

(21) Appl. No.: 12/543,022

(22) Filed: Aug. 18, 2009

(65) Prior Publication Data

US 2010/0105893 A1    Apr. 29, 2010

(30) Foreign Application Priority Data

Aug. 20, 2008  (JP) ................. P2008-211875

(51) Int. Cl.
  *C07D 201/04* (2006.01)
(52) U.S. Cl. ...................................... 540/536
(58) Field of Classification Search ................... 540/536
  See application file for complete search history.

(56) References Cited

U.S. PATENT DOCUMENTS

| 4,968,793 | A | 11/1990 | Kitamura et al. |
| 6,303,099 | B1 | 10/2001 | Ichihashi et al. |

FOREIGN PATENT DOCUMENTS

| EP | 1065167 A1 | 1/2001 |
| EP | 1614657 A2 | 1/2006 |
| JP | 2275850 A | 11/1990 |
| JP | 05-170732 A | 7/1993 |
| JP | 2001-072411 A | 3/2001 |
| WO | 2004080889 A2 | 9/2004 |

OTHER PUBLICATIONS

EP Extended Search Report issued on Sep. 16, 2010 in EP Application No. 09252014.7.
Larry W. Beck et al. "Alkylammonium polycations as structure-directing agents in MFI zeolite synthesis," Microporous and Mesoporous Materials, vol. 22, p. 107-114 (1998).
Timothy O. Drews et al. "Progress in manipulating zeolite morphology and related applications," Current Opinion in Colloid and Interface Science, vol. 10, p. 233-238 (2005).
E. De Vos Burchart, "Molecular mechanics studies and MFI-type zeolites: Part 4. Energetics of crystal growth directing agents," Zeolites, vol. 13, p. 216-221 (1993).
Isabel Diaz et al., "Surface Structure of Zeolite (MFI) Crystals," Chem. Mater., vol. 16, No. 25, pp. 5226-5232, (2004).
Griselda Bonilla, et al., "Zeolite (MFI) Crystal Morphology Control Using Organic Structure-Directing Agents," Chem. Mater., vol. 16, No. 26, pp. 5697-5705, (2004).

*Primary Examiner* — Bruck Kifle
(74) *Attorney, Agent, or Firm* — Panitch Schwarze Belisario & Nadel LLP

(57) ABSTRACT

The present invention provides a method which can produce ε-caprolactam with a good selectivity by reacting cyclohexanone oxime with a good conversion in a vapor phase Beckmann rearrangement reaction. Disclosed is a method for producing ε-caprolactam, which comprises performing a vapor phase Beckmann rearrangement reaction of cyclohexanone oxime in the presence of a pentasil type zeolite, wherein the pentasil type zeolite is a zeolite obtained by subjecting a mixture containing a silicon compound, water, and a compound represented by formula (I):

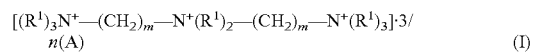

$$[(R^1)_3N^+\text{—}(CH_2)_m\text{—}N^+(R^1)_2\text{—}(CH_2)_m\text{—}N^+(R^1)_3]\cdot 3/n(A) \quad (I)$$

wherein $R^1$ represents an alkyl group having 1 to 4 carbon atoms, A represents an n-valent anion, m represents an integer of 5 to 7, and n represents an integer of 1 to 3, to a hydrothermal synthesis reaction.

4 Claims, 1 Drawing Sheet

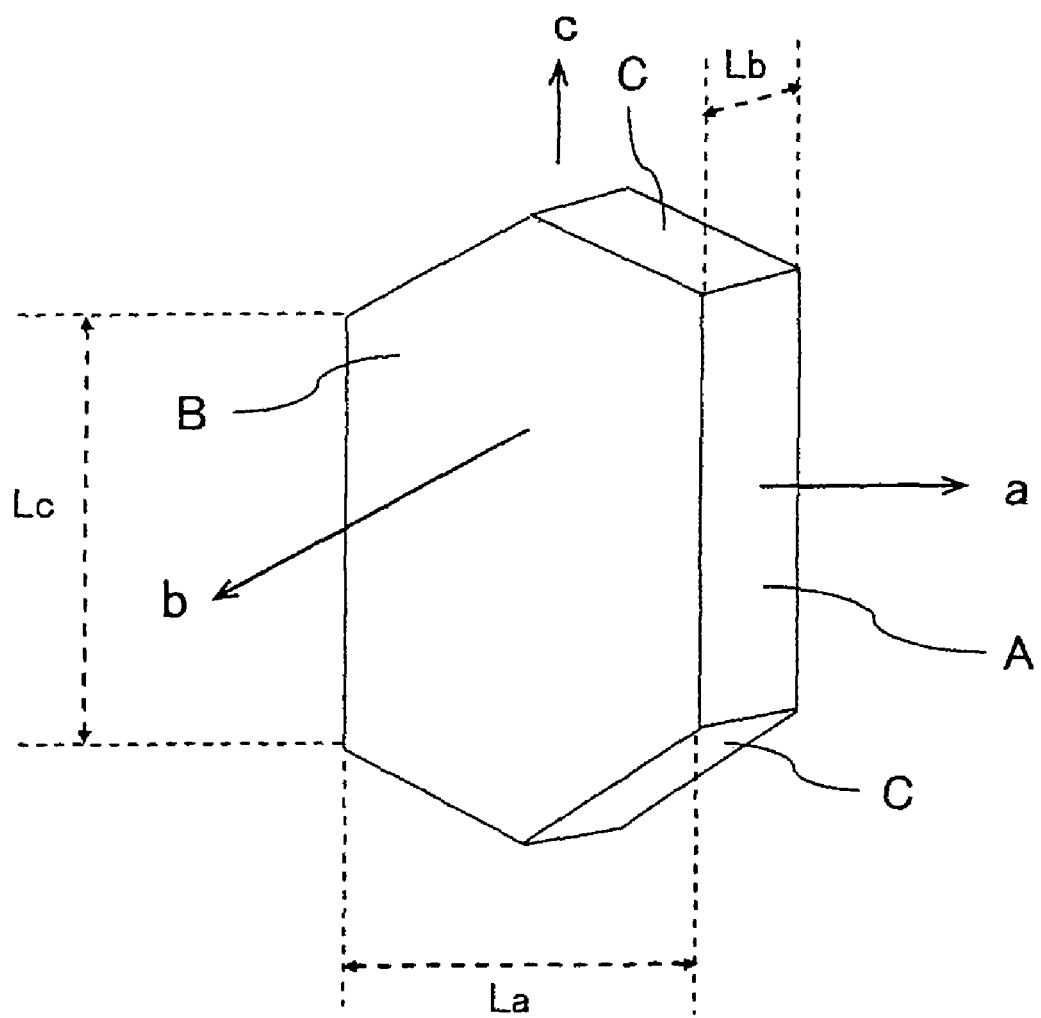

METHOD FOR PRODUCING ε-CAPROLACTAM AND METHOD FOR PRODUCING PENTASIL TYPE ZEOLITE

BACKGROUND OF THE INVENTION

1. Field of the Invention

The present application is filed, claiming the Paris Convention priorities of Japanese Patent Application No. 2008-211875 (filed on Aug. 20, 2008), the entire content of which is incorporated herein by reference.

The present invention relates to a method for producing ε-caprolactam by performing a vapor phase Beckmann rearrangement reaction of cyclohexanone oxime in the presence of a pentasil type zeolite. The present invention also relates to a method for producing a pentasil type zeolite, which is suited for the method for producing ε-caprolactam.

2. Description of the Related Art

As a method for producing ε-caprolactam by performing a vapor phase Beckmann rearrangement reaction of cyclohexanone oxime in the presence of a pentasil type zeolite, there is a method using a pentasil type zeolite obtained by subjecting a mixture of a silicon compound, water and a tetra-n-propylammonium salt to a hydrothermal synthesis reaction (see, for example, Japanese Unexamined Patent Publication (Kokai) No. 2007-222758, Japanese Unexamined Patent Publication (Kokai) No. 2003-176125, Japanese Unexamined Patent Publication (Kokai) No. 2001-72411, Japanese Unexamined Patent Publication (Kokai) No. H11-57483, Japanese Unexamined Patent Publication (Kokai) No. H05-170732, Japanese Unexamined Patent Publication (Kokai) No. 1102-275850 and Japanese Unexamined Patent Publication (Kokai) No. 1102-250866).

However, the above conventional methods were not necessarily satisfactory in terms of a conversion of cyclohexanone oxime and a selectivity of ε-caprolactam.

SUMMARY OF THE INVENTION

Thus, an object of the present invention is to provide a method which can produce ε-caprolactam with a good selectivity by reacting cyclohexanone oxime with a good conversion in a vapor phase Beckmann rearrangement reaction. Another object of the present invention is to provide a method for producing a pentasil type zeolite which can impart a good conversion and selectivity in the Beckmann rearrangement reaction.

Under these circumstances, the present inventors have intensively studied and found a method for producing ε-caprolactam and a method for producing a pentasil type zeolite, which can achieve the above objects. Thus, the present invention has been completed.

The present invention provides a method for producing ε-caprolactam and a method for producing a pentasil type zeolite shown below.

[1] A method for producing ε-caprolactam, which comprises performing a vapor phase Beckmann rearrangement reaction of cyclohexanone oxime in the presence of a pentasil type zeolite, wherein the pentasil type zeolite is a zeolite obtained by subjecting a mixture containing a silicon compound, water, and a compound represented by formula (I):

$$[(R^1)_3N^+\text{—}(CH_2)_m\text{—}N^+(R^1)_2\text{—}(CH_2)_m\text{—}N^+(R^1)_3] \cdot 3/n(A) \quad (I)$$

wherein $R^1$ represents an alkyl group having 1 to 4 carbon atoms, A represents an n-valent anion, m represents an integer of 5 to 7, and n represents an integer of 1 to 3, to a hydrothermal synthesis reaction.

[2] A method for producing ε-caprolactam, which comprises performing a vapor phase Beckmann rearrangement reaction of cyclohexanone oxime in the presence of a pentasil type zeolite, wherein the pentasil type zeolite is a zeolite obtained by subjecting a mixture containing a silicon compound, water, and a compound represented by formula (II):

$$[(R^2)_3N^+\text{—}(CH_2)_j\text{—}N^+(R^2)_3] \cdot 2/k(B) \quad (II)$$

wherein $R^2$ represents an alkyl group having 1 to 4 carbon atoms, B represents a k-valent anion, j represents an integer of 5 to 7, and k represents an integer of 1 or 2, to a hydrothermal synthesis reaction.

[3] A method for producing a pentasil type zeolite, which comprises subjecting a mixture containing a silicon compound, water, a tetraalkyl ammonium salt, and a compound represented by formula (I):

$$[(R^1)_3N^+\text{—}(CH_2)_m\text{—}N^+(R^1)_2\text{—}(CH_2)_m\text{—}N^+(R^1)_3] \cdot 3/n(A) \quad (I)$$

wherein $R^1$ represents an alkyl group having 1 to 4 carbon atoms, A represents an n-valent anion, m represents an integer of 5 to 7, and n represents an integer of 1 to 3, to a hydrothermal synthesis reaction.

[4] A method for producing a pentasil type zeolite, which comprises subjecting a mixture containing a silicon compound, water, a tetraalkyl ammonium salt, and a compound represented by formula (II):

$$[(R^2)_3N^+\text{—}(CH_2)_j\text{—}N^+(R^2)_3] \cdot 2/k(B) \quad (II)$$

wherein $R^2$ represents an alkyl group having 1 to 4 carbon atoms, B represents a k-valent anion, j represents an integer of 5 to 7, and k represents an integer of 1 or 2, to a hydrothermal synthesis reaction.

According to the present invention, ε-caprolactam can be produced with a good selectivity by reacting cyclohexanone oxime with a good conversion in a vapor phase Beckmann rearrangement reaction. Also, a pentasil type zeolite, which can impart a good conversion and selectivity in the Beckmann rearrangement reaction, can be provided.

BRIEF DESCRIPTION OF THE DRAWINGS

FIG. 1 is a schematic view for explaining a shape of a primary particle of a pentasil type zeolite.

DETAILED DESCRIPTION OF THE INVENTION

The present invention will be explained in detail below. In the present invention, using a pentasil type zeolite as a catalyst, ε-caprolactam is produced by performing a vapor phase Beckmann rearrangement reaction of cyclohexanone oxime in the presence of the pentasil type zeolite. The pentasil type zeolite as used herein contains silicon and oxygen as elements constituting the framework and may be a crystalline silica whose framework is substantially composed of silicon and oxygen, or may be a crystalline metallosilicate or the like which further contains another metal element (hereinafter referred to as "Me") as an element constituting the framework. In the case of the crystalline metallosilicate, examples of an element (Me) other than silicon and oxygen that may exist include Be, B, Al, Ti, V, Cr, Fe, Co, Ni, Cu, Zn, Ga, Ge, Zr, Nb, Sb, La, Hf, Bi and the like and, if necessary, the crystalline metallosilicate may contain two or more of them. The pentasil type zeolite is preferably a zeolite having a MFI structure, and ZSM-5 and ZSM-11 types are particularly preferred. It can be confirmed by a measurement of XRD (X-ray diffraction) whether or not a pentasil type zeolite structure exists.

When the pentasil type zeolite also contains a metal element (Me) other than silicon and oxygen, an atomic ratio of a silicon element (Si) to the metal element (Me) that satisfies the following relation: Si/Me≧500 is preferred in terms of a conversion and a selectivity.

In the present invention, the pentasil type zeolite is prepared by subjecting a mixture containing a silicon compound, water and a predetermined structure-directing agent to a hydrothermal synthesis reaction. As the structure-directing agent used for the hydrothermal synthesis reaction, for example, used is a compound represented by the following formula (I)

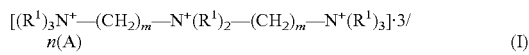
$$[(R^1)_3N^+—(CH_2)_m—N^+(R^1)_2—(CH_2)_m—N^+(R^1)_3]\cdot 3/n(A) \quad (I)$$

wherein $R^1$ represents an alkyl group having 1 to 4 carbon atoms, A represents an n-valent anion, m represents an integer of 5 to 7, and n represents an integer of 1 to 3 (hereinafter referred to as "compound (I)"), or a compound represented by formula (II):

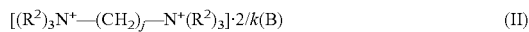
$$[(R^2)_3N^+—(CH_2)_j—N^+(R^2)_3]\cdot 2/k(B) \quad (II)$$

wherein $R^2$ represents an alkyl group having 1 to 4 carbon atoms, B represents a k-valent anion, j represents an integer of 5 to 7, and k represents an integer of 1 or 2 (hereinafter referred to as "compound (II)"). In the present invention, a pentasil type zeolite, which can impart a good conversion and selectivity in a vapor phase Beckmann rearrangement reaction of cyclohexanone oxime by performing a hydrothermal synthesis using a compound (I) or a compound (II) as a structure-directing agent, can be produced. Each of the compound (I) or the compound (II) may be used alone, or two or more of the compounds (I) or (II) may be used together. Furthermore, the compound (I) and the compound (II) may be used in combination as the structure-directing agent.

As the structure-directing agent, a tetraalkyl ammonium salt can also be used in addition to the compound (I) and/or the compound (II). In the present invention, it is effective to use the tetraalkyl ammonium salt in combination, in addition to the compound (I) and/or the compound (II), in order to control a shape of a primary particle of a pentasil type zeolite.

As the silicon compound, for example, tetraalkyl orthosilicate such as tetramethyl orthosilicate, tetraethyl orthosilicate, tetrapropyl orthosilicate, tetrabutyl orthosilicate or the like is preferred and, if necessary, two or more silicon compounds can also be used. Among these silicon compounds, tetraethyl orthosilicate is more preferred.

In the compound (I), $R^1$ represents an alkyl group having 1 to 4 carbon atoms and examples thereof include a methyl group, an ethyl group, an n-propyl group, an iso-propyl group, an n-butyl group, an s-butyl group and a t-butyl group. Among these alkyl groups, an n-propyl group is preferred. In the compound (I), A represents an n-valent anion and examples thereof include a monovalent anion such as hydroxide ion, halogen ion (e.g. fluoride ion, bromide ion, iodide ion, etc.), alkoxide ion, nitric acid ion, perchlorate ion, chlorate ion or the like; and a divalent or trivalent anion, such as carbonate ion, phosphate ion, sulfate ion, tungstate ion, chromate ion, ferricyanide ion, silicate ion or the like. Among these n-valent anions, hydroxide ion and halogen ion are preferred.

In the compound (II), $R^2$ represents an alkyl group having 1 to 4 carbon atoms and examples thereof may include the same alkyl groups as described above for $R^1$. Among these alkyl groups, an n-propyl group is preferred. In the compound (II), B represents a k-valent anion and examples thereof include a monovalent anion such as hydroxide ion, halogen ion (e.g. fluoride ion, bromide ion, iodide ion, etc.), alkoxide ion, nitric acid ion, perchlorate ion, chlorate ion or the like; and a divalent anion such as carbonate ion, sulfate ion, tungstate ion, chromate ion, silicate ion or the like. Among these k-valent anions, hydroxide ion and halogen ion are preferred.

Examples of the tetraalkyl ammonium salt include a halide, hydroxide, sulfate and nitrate of tetraalkyl ammonium such as teteramethyl ammonium, teteraethyl ammonium, n-propyltrimethyl ammonium, tetra-n-propyl ammonium, tetra-n-butyl ammonium or the like. If necessary, two or more of them can also be used. Among these, a tetra-n-propyl ammonium salt is preferred.

In the present invention, as a structure-directing agent in a hydrothermal synthesis reaction, a compound (I) and/or a compound (II) is used, or a compound (I) or a compound (II) is used in combination with a tetraalkyl ammonium salt. Thus, by using such a predetermined structure-directing agent, a shape of a primary particle of the obtained pentasil type zeolite can be controlled.

As shown in a schematic view of FIG. 1, usually, a primary particle of a pentasil type zeolite is typically represented by a coffin shape consisting of two surfaces A, two surfaces B and four surfaces C. When a direction substantially vertical to the surface A (direction indicated by an arrow a in FIG. 1) is an a axial direction, a direction substantially vertical to the surface B (direction indicated by an arrow b in FIG. 1) is a b axial direction, a direction substantially vertical to the surface C (direction indicated by an arrow c in FIG. 1) is a c axial direction, and lengths in these axial directions are respectively La, Lb and Lc, lengths La, Lb and Lc in these axial directions satisfy the following relation: Lc>La>Lb in a pentasil type zeolite whose structure is defined only by a conventional tetra-n-propylammonium salt.

In contrast, a use of a compound (I) in which $R^1$ is an n-propyl group, m is 6, A is an hydroxide ion or an iodide ion, and n is 1 (hereinafter may be referred to as "$tC_6.OH^-$" or "$tC_6.I^-$") as a structure-directing agent for a hydrothermal synthesis reaction enables lengths in axial directions to satisfy the following relation: Lc>Lb>La, and thus making it possible to prepare a primary particle having a wide surface A. Furthermore, by using $tC_6.OH^-$ or $tC_6.I^-$ in combination with a tetra-n-propylammonium salt, lengths in each axial direction (particularly, a ratio La/Lb) can be controlled.

Also, a use of a compound (II) in which $R^2$ is an n-propyl group, j is 5, B is an hydroxide ion or an iodide ion, and k is 1 (hereinafter may be referred to as "$dC_5.OH^-$" or "$dC_5.I^-$") as a structure-directing agent for a hydrothermal synthesis reaction enables lengths in axial directions to satisfy the following relation: La>Lc>Lb, and thus making it possible to prepare a primary particle having a wide surface B. Furthermore, by using $dC_5.OH^-$ or $dC_5.I^-$ in combination with a tetra-n-propyl ammonium salt, lengths in these axial directions can be controlled.

A shape of a primary particle such as lengths in axial directions can be analyzed by a scanning electron microscope (SEM).

When a hydrothermal synthesis reaction is performed, the pH of a mixture subjected to the hydrothermal synthesis reaction can also be controlled by adding inorganic bases, for example, alkali metal hydroxides such as lithium hydroxide, sodium hydroxide and potassium hydroxide; alkali earth metal hydroxides such as magnesium hydroxide and calcium hydroxide; alkali metal carbonates such as sodium carbonate, potassium carbonate and cesium carbonate; alkali metal bicarbonates such as sodium hydrogen carbonate and potassium hydrogen carbonate; alkali metal acetates such as sodium acetate and potassium acetate; and alkali metal phosphates such as sodium phosphate. Particularly when A in the compound (I) or B in the compound (II) is not a hydroxide ion, it is effective to perform the hydrothermal synthesis reaction with adding alkali metal hydroxides because it is possible to produce a pentasil type zeolite which can impart a good conversion and selectivity in the vapor phase Beckmann reaction.

When a hydrothermal synthesis reaction is performed, the used amount of water is usually from 5 to 1000 mol, and preferably from 10 to 300 mol per mol of a silicon compound. The used amount of a compound (I) or a compound (II) is usually from 0.0001 to 1.0 mol, and preferably from 0.001 to 0.5 mol per mol of a silicon compound. When a tetraalkyl ammonium salt is used in combination, the used amount thereof is usually from 0.0001 to 1.0 mol, and preferably from 0.001 to 0.5 mol per mol of a silicon compound. When a compound (I) or a compound (II) is used in combination with a tetraalkyl ammonium salt, a ratio of them may be appropriately set considering that lengths in each axial direction of a primary particle of the obtained pentasil type zeolite are controlled as described above. When the inorganic bases described above are used, the used amount thereof is usually from 0.001 to 1.2 mol, and preferably from 0.01 to 0.5 mol per mol of a silicon compound.

The reaction temperature in the hydrothermal synthesis reaction is usually from about 80 to 200° C., and the reaction time is usually from about 1 to 240 hours.

A slurry containing a pentasil type zeolite can be obtained by the hydrothermal synthesis reaction described above. The pentasil type zeolite is usually used for the vapor phase Beckmann rearrangement reaction of cyclohexanone oxime after obtained from the slurry by separation. Herein, examples of the method in which the pentasil type zeolite is obtained from the slurry by separation include a method in which a liquid phase is removed by distillation from the slurry and a method in which a liquid phase is removed by a solid-liquid separation of the slurry, typically through filtration or decantation and the like. Among these methods, the method in which a solid-liquid separation of the slurry is performed by filtration or decantation is preferred since the removed liquid phase can be used again for the hydrothermal synthesis reaction (so-called recycling). When the liquid phase is recycled, the above described silicon compound, water and structure-directing agent (compound (I), compound (II) and tetraalkyl ammonium salt) can be added to the liquid phase, if necessary. When the liquid phase is recycled, it is more effective to use those purified by distillation while maintaining an active ingredient (silicon source) contained in the liquid phase.

The pentasil type zeolite separated as described above can be used as it is for a vapor phase Beckmann rearrangement reaction, but is preferably further washed, or dried and calcined under an atmosphere of nitrogen, air or a mixed gas thereof. It is particularly effective to calcine so as to remove the structure-directing agent used for the hydrothermal synthesis reaction. Examples of a washing liquid that may be used for washing include water, or acidic water such as hydrochloric acid (aqueous solution of hydrogen chloride), aqueous solution of sulfuric acid, aqueous solution of nitric acid or the like. In the case of drying, the drying temperature is usually from about 50 to 200° C. and the drying time is usually from about 1 to 100 hours. In the case of calcining, the calcining temperature is usually from about 400 to 600° C. and the calcining time is usually from about 1 to 100 hours.

It is possible to improve the catalyst life for the vapor phase Beckmann rearrangement reaction of the pentasil type zeolite that was washed, dried and/or calcined as described above by further contacting such zeolite with an aqueous solution of ammonia, and drying.

The pH of the aqueous solution of ammonia that may be used is usually 9 or more, and preferably from 10 to 13. The concentration of ammonia in the aqueous solution is usually from 2 to 30 wt %, and preferably from 5 to 25 wt %.

The aqueous solution, which further contains an ammonium salt is preferred. Examples of the preferred ammonium salt include ammonium nitrate, ammonium chloride, ammonium sulfate and the like and, if necessary, two or more ammonium salts can be used. Among these ammonium salts, ammonium nitrate is more preferred. The amount of the ammonium salt is usually from 0.001 to 1 mol, and preferably from 0.01 to 0.1 mol per mol of ammonia.

If necessary, the aqueous solution may contain an ammonium salt other than those described above. Examples thereof include halides, sulfates and nitrates of tetramethyl ammonium, tetraethyl ammonium, n-propyltrimethyl ammonium, tetra-n-propyl ammonium, tetra-n-butyl ammonium, 4,4'-trimethylenebis(dimethylpiperidium), benzyltrimethyl ammonium, dibenzyldimethyl ammonium, 1,1'-butylenebis(4-aza-1-azoniabicyclo[2,2,2]octane), trimethyladamantyl ammonium and the like. If necessary, two or more ammonium salts can also be used. Among these ammonium salts, halide of tetraalkyl ammonium, such as tetra-n-propyl ammonium bromide is preferred.

The contact treatment with ammonia may be performed batchwise or continuously. For example, the catalyst may be immersed in the aqueous solution of ammonia in a stirring tank, and stirred, or the aqueous solution of ammonia may be passed through a tubular container filled with the catalyst. The temperature of the contact treatment with ammonia is usually from 50 to 250° C., preferably from 50 to 200° C., and still more preferably from 60 to 150° C. The contact treatment with ammonia is usually conducted for from 0.1 to 10 hours. The amount of the aqueous solution that may be used is usually from 100 to 5,000 parts by weight per 100 parts by weight of the pentasil type zeolite.

If necessary, the contact treatment with ammonia may be performed more than once. If necessary, prior to the contact treatment with ammonia, a steam contact treatment of bringing into contact with steam may be performed. Furthermore, these contact treatments may be performed in combination with a known contact treatment such as those described in Japanese Unexamined Patent Publication (Kokai) No. H05-170732 (Patent Document 5), or the like.

Thus, the pentasil type zeolite can be produced. ε-caprolactam can be produced with a good conversion and selectivity by performing a vapor phase Beckmann rearrangement reaction of cyclohexanone oxime in the presence of the zeolite. The zeolite can be used for the above reaction as it is, and a zeolite molded by a conventionally known method may also be used.

In the Beckmann rearrangement reaction, the reaction temperature is usually from 250 to 500° C., and preferably from 300 to 450° C. The reaction pressure is usually from 0.005 to 0.5 MPa, and preferably from 0.005 to 0.2 MPa. The reaction may be performed by a fixed bed or fluidized bed system. The supply rate of cyclohexanone oxime as a starting material is usually from 0.1 to 20 $h^{-1}$, and preferably from 0.2 to 10 $h^{-1}$ as a supply rate (kg/h) per 1 kg of the pentasil type zeolite (catalyst), namely, a space velocity WHSV ($h^{-1}$).

When the Beckmann rearrangement reaction is performed, in view of an improvement in a conversion of cyclohexanone oxime and a selectivity of ε-caprolactam, an alcohol is preferably allowed to coexist. The alcohol usually has 1 to 8 carbon atoms, and preferably 1 to 6 carbon atoms. Examples thereof include methanol, ethanol, 1-propanol, 2-propanol, 1-butanol, 1-methyl-1-propanol, 2-methyl-1-propanol, 1-pentanol, 1-hexanol and the like and, if necessary, two or more of the alcohols can also be used. Among these alcohols, methanol and ethanol are preferred. The used amount of the alcohol is usually from 10 to 2,000 parts by weight, and preferably from 20 to 1,000 parts by weight per 100 parts by weight of cyclohexanone oxime.

When the Beckmann rearrangement reaction is performed, water may be allowed to coexist. In this case, the used amount of water is preferably 2.5 mol or less per mol of cyclohexanone oxime. Furthermore, when the Beckmann rearrangement reaction is performed, an inert gas may be allowed to coexist and examples of the inert gas include for example, nitrogen, argon, carbon dioxide and the like.

The Beckmann rearrangement reaction may be performed in combination with an operation of calcining a pentasil type zeolite (catalyst) under atmosphere of an oxygen-containing gas such as air or the like. By this calcining treatment, a carbonaceous substance precipitated out on the pentasil type zeolite (catalyst) can be removed by combustion, and also a conversion of cyclohexanone oxime and a persistence of a selectivity of ε-caprolactam can be enhanced. For example, when the reaction is performed by a fixed bed system, there can be preferably employed a method of supplying cyclohexanone oxime to a fixed bed type reactor filled with a pentasil type zeolite (catalyst), optionally together with an alcohol, water, an inert gas or the like, performing a reaction for a predetermined time, followed by stopping the supply of cyclohexanone oxime, and then supplying an oxygen-containing gas to calcine, and further repeating the reaction and the calcination. When the reaction is performed by a fluidized bed system, there can be preferably employed a method of supplying cyclohexanone oxime to a fluidized bed type reactor in which a solid catalyst flows, optionally together with an alcohol, water, an inert gas or the like, and continuously or intermittently extracting the pentasil type zeolite (catalyst) from the reactor while reacting, followed by calcining the zeolite in a calcining device and returning the zeolite to the reactor again.

As a post-treatment operation of a reaction mixture obtained by such Beckmann rearrangement reaction, a suitable known method can be employed. For example, ε-caprolactam can be separated by cooling reaction product gas to condense it and subjecting the resulting to operations such as extraction, distillation, crystallization and the like.

EXAMPLES

Examples of the present invention will be described below, but the present invention is not limited by these Examples.

A space velocity WHSV ($h^{-1}$) of cyclohexanone oxime was calculated by dividing a supply rate (g/h) of cyclohexanone oxime by an amount (g) of a catalyst (zeolite).

Production Example 1

Production of Compound (I) ($tC_6.I^-$)

The compound (I) represented by the general formula (I) in which $R^1$ is an n-propyl group, m is 6, A is an iodide ion and n is 1, namely, a compound ($tC_6.I^-$) represented by $[(C_3H_7)_3N^+—(CH_2)_6—N^+(C_3H_7)_2—(CH_2)_6—N^+(C_3H_7)_3]·3I^-$ was produced as follows.

In a 500 ml three-necked flask, 178 parts by weight of ethanol, 15.5 parts by weight of bis(hexamethylene)triamine, 36.3 parts by weight of potassium carbonate and 109 parts by weight of 1-iodopropane were charged, stirred under shade and reflux conditions at 80° C. for 24 hours and left to cool to room temperature, and then the obtained reaction mixture was filtered. The obtained filtrate was sufficiently concentrated under reduced pressure at 50° C. to obtain a product having a high viscosity. The obtained product was redissolved by adding 100 parts by weight of ethanol and the remaining impurities were removed by filtration. The obtained filtrate was recrystallized by adding 400 parts by weight of ethyl acetate and filtered, and then the residue was air-dried to obtain 46 parts by weight of a crystal of $tC_6.I^-$.

Production Example 2

Production of Compound (I) ($tC_6.OH^-$)

The compound (I) represented by the general formula (I) in which $R^1$ is an n-propyl group, m is 6, A is a hydroxide ion and n is 1, namely, a compound ($tC_6.OH^-$) represented by $[(C_3H_7)_3N^+—(CH_2)_6—N^+(C_3H_7)_2—(CH_2)_6—N^+(C_3H_7)_3]·3OH^-$ was produced as follows.

In a 500 ml beaker, 35 parts by weight of $tC_6.I^-$ obtained in Production Example 1, 65 parts by weight of water and 141 parts by weight of a strong basic anion exchange resin ("Duolite® UP5000", manufactured by Rohm and Haas Company) were charged and stirred at room temperature for 24 hours, and then the ion exchange resin was removed by filtration to obtain an aqueous 26 wt % solution of $tC_6.OH^-$.

Example 1

Production of Pentasil Type Zeolite (1)

In an autoclave made of stainless steel, 5.6 parts by weight of tetraethyl orthosilicate ($Si(OC_2H_5)_4$), 1.0 parts by weight of the crystal of $tC_6.I^-$ obtained in Production Example 1, 6.5 parts by weight of an aqueous 5.6 wt % potassium hydroxide solution and 86.9 parts by weight of water were charged and stirred at room temperature for 24 hours, and then a hydrothermal synthesis reaction was carried out by stirring at 175° C. for 72 hours. The obtained slurry (reaction mixture) was filtered and the residue was continuously washed with ion exchanged water until the pH of the wash became around 7, and dried at 60° C.

The obtained dried product was calcined under nitrogen flow at 530° C. for 1 hour, and then calcined under air flow at 530° C. for 1 hour to obtain a powdery white crystal. This powdery white crystal was analyzed by powder X-ray diffraction. As a result, it was identified as a zeolite having a MFI structure.

Then, 1.4 g of the obtained powdery white crystal was charged in an autoclave and a mixture of a solution (pH=11.5) of 18 g of an aqueous 7.5 wt % ammonium nitrate solution and 28 g of an aqueous 25 wt % ammonia solution was added and, after stirring at 90° C. for 1 hour, a crystal was separated by filtration. This crystal was subjected to the same treatment as the above (namely, a treatment of adding a mixture of a solution of an aqueous ammonium nitrate solution and an aqueous ammonia solution, and stirring and filtration) further twice, washed with water and dried to obtain a pentasil type zeolite (1).

Production of ε-Caprolactam

A reaction tube having an inner diameter of 1 cm made of quartz glass was filled with 0.5 g of the pentasil type zeolite (1) obtained above as a catalyst to form a catalyst layer and a preheating treatment was performed under nitrogen flow (4.2

L/h) at 350° C. for 1 hour. After a temperature of the catalyst layer was raised to 366° C. under nitrogen flow (4.2 L/h), a vaporized mixed gas of cyclohexanone oxime/methanol in a weight ratio of 1/3.6 was supplied to the reaction tube at a supply rate of 1.4 g/h (a space velocity WHSV of cyclohexanone oxime=0.6 h$^{-1}$) and a vapor phase Beckmann rearrangement reaction of cyclohexanone oxime was performed.

For 4 to 6 hours after the beginning of the reaction, the reaction gas was collected and an amount of the unreacted cyclohexanone oxime contained in the gas collected in this 2 hours and an amount of the produced ϵ-caprolactam were measured by gas chromatography, and then a conversion of cyclohexanone oxime and a selectivity of ϵ-caprolactam were respectively calculated by the following equations:

Conversion (%) of cyclohexanone oxime=[(X−Y)/X]×100

Selectivity (%) of ϵ-caprolactam=[Z/(X−Y)]×100 where X denotes a mol number of cyclohexanone oxime supplied for 2 hours, Y denotes a mol number of the unreacted cyclohexanone oxime, and Z denotes a mol number of the produced ϵ-caprolactam.

As a result, the conversion of cyclohexanone oxime was 95.8% and the selectivity of ϵ-caprolactam was 89.5%.

Example 2

Production of Pentasil Type Zeolite (2)

In an autoclave made of stainless steel, 5.6 parts by weight of tetraethyl orthosilicate (Si(OC$_2$H$_5$)$_4$), 0.2 part by weight of the crystal of tC$_6$.I$^-$ obtained in Production Example 1, 1.0 part by weight of tetra-n-propylammonium iodide, 6.5 parts by weight of an aqueous 5.6 wt % potassium hydroxide solution and 86.9 parts by weight of water were charged and stirred at room temperature for 24 hours, and then a hydrothermal synthesis reaction was carried out by stirring at 175° C. for 72 hours. The obtained slurry (reaction mixture) was filtered and the residue was continuously washed with ion exchanged water until the pH of the wash became around 7, and dried at 60° C.

The obtained dried product was calcined under nitrogen flow at 530° C. for 1 hour and calcined under air flow at 530° C. for 1 hour to obtain a powdery white crystal. This powdery white crystal was analyzed by powder X-ray diffraction. As a result, it was identified as a zeolite having a MFI structure.

Then, 1.4 g of the obtained powdery white crystal was charged in an autoclave and a treatment of adding a solution that is a mixture of an aqueous ammonium nitrate solution and an aqueous ammonia solution, and of stirring and filtration was repeated three times in total in the same manner as in Example 1, and then washed with water and dried to obtain a pentasil type zeolite (2).

Production of ϵ-Caprolactam

In the same manner as in Example 1, except that a catalyst layer was formed by filling with 0.5 g of the pentasil type zeolite (2) obtained above as a catalyst, a vapor phase Beckmann rearrangement reaction of cyclohexanone oxime was performed.

For 4 to 6 hours after the beginning of the reaction, the reaction gas was collected, and then a conversion of cyclohexanone oxime and a selectivity of ϵ-caprolactam were determined in the same manner as in Example 1. As a result, the conversion of cyclohexanone oxime was 91.2% and the selectivity of ϵ-caprolactam was 92.9%.

Example 3

Production of Pentasil Type Zeolite (3)

In an autoclave made of stainless steel, 55 parts by weight of tetraethyl orthosilicate (Si(OC$_2$H$_5$)$_4$), 37 parts by weight of an aqueous 26 wt % solution of tC$_6$.OH$^-$ obtained in Production Example 2 and 144 parts by weight of water were charged and vigorously stirred at room temperature for 120 minutes, and then a hydrothermal synthesis reaction was carried out by stirring at 150° C. for 72 hours. The obtained slurry (reaction mixture) was filtered and the residue was continuously washed with ion exchanged water until the pH of the wash became around 9, and dried at 110° C.

The obtained dried product was calcined under nitrogen flow at 530° C. for 1 hour, and then calcined under air flow at 530° C. for 1 hour to obtain a powdery white crystal. This powdery white crystal was analyzed by powder X-ray diffraction. As a result, it was identified as a zeolite having a MFI structure.

Then, 3.5 g of the obtained powdery white crystal was charged in an autoclave and a solution (pH=11.5) that is a mixture of 38.5 g of an aqueous 7.5 wt % ammonium nitrate solution and 59 g of an aqueous 25 wt % ammonia solution was added and, after stirring at 90° C. for 1 hour, a crystal was separated by filtration. This crystal was subjected to the same treatment as the above (namely, a treatment of adding a solution that is a mixture of an aqueous ammonium nitrate solution and an aqueous ammonia solution, and stirring and filtration) further twice, washed with water and dried to obtain a pentasil type zeolite (3).

Production of ϵ-Caprolactam

A reaction tube having an inner diameter of 1 cm made of quartz glass was filled with 0.375 g of the pentasil type zeolite (3) obtained above as a catalyst to form a catalyst layer and a preheating treatment was performed under nitrogen flow (4.2 L/h) at 350° C. for 1 hour. After a temperature of the catalyst layer was lowered to 327° C. under nitrogen flow (4.2 L/h), a vaporized mixed gas of cyclohexanone oxime/methanol in a weight ratio of 1/1.8 was supplied to the reaction tube at a supply rate of 8.4 g/h (a space velocity WHSV of cyclohexanone oxime=8 h$^{-1}$) and a vapor phase Beckmann rearrangement reaction of cyclohexanone oxime was performed.

For 5.5 to 5.75 hours after the beginning of the reaction, the reaction gas was collected and an amount of the unreacted cyclohexanone oxime contained in the gas collected in this 0.25 hour and an amount of the produced ϵ-caprolactam were measured by gas chromatography, and then a conversion of cyclohexanone oxime and a selectivity of ϵ-caprolactam were respectively calculated by the same equations as in Example 1. In the equations, X denotes a mol number of cyclohexanone oxime supplied for 0.25 hours, Y denotes a mol number of the unreacted cyclohexanone oxime, and Z denotes a mol number of the produced ϵ-caprolactam. As a result, the conversion of cyclohexanone oxime was 99.9% and the selectivity of ϵ-caprolactam was 96.2%.

Example 4

Production of Pentasil Type Zeolite (4)

In an autoclave made of stainless steel, 55 parts by weight of tetraethyl orthosilicate (Si(OC$_2$H$_5$)$_4$), 6.2 parts by weight of an aqueous 26 wt % solution of tC$_6$.OH$^-$ obtained in Production Example 2, 20.2 parts by weight of an aqueous 40 wt % tetra-n-propylammonium hydroxide solution and 155 parts by weight of water were charged and vigorously stirred at room temperature for 120 minutes, and then a hydrothermal synthesis reaction was carried out by stirring at 150° C. for 72 hours. The obtained slurry (reaction mixture) was filtered and the residue was continuously washed with ion exchanged water until the pH of the wash became around 9, and dried at 110° C.

The obtained dried product was calcined under nitrogen flow at 530° C. for 1 hour, and then calcined under air flow at 530° C. for 1 hour to obtain a powdery white crystal. This powdery white crystal was analyzed by powder X-ray diffraction. As a result, it was identified as a zeolite having a MFI structure.

Then, 3.5 g of the obtained powdery white crystal was charged in an autoclave and a treatment of adding a solution that is a mixture of an aqueous ammonium nitrate solution and an aqueous ammonia solution, and stirring and filtration was repeated three times in total in the same manner as in Example 3, and then washed with water and dried to obtain a pentasil type zeolite (4).

Production of ε-Caprolactam

In the same manner as in Example 3, except that a catalyst layer was formed by filling with 0.375 g of the pentasil type zeolite (4) obtained above as a catalyst, a vapor phase Beckmann rearrangement reaction of cyclohexanone oxime was performed.

For 5.5 to 5.75 hours after the beginning of the reaction, the reaction gas was collected and a conversion of cyclohexanone oxime and a selectivity of ε-caprolactam were determined in the same manner as in Example 3. As a result, the conversion of cyclohexanone oxime was 99.2% and the selectivity of ε-caprolactam was 96.2%.

Comparative Example 1

Production of Comparative Pentasil Type Zeolite (C1)

In an autoclave made of stainless steel, 15.9 parts by weight of tetraethyl orthosilicate ($Si(OC_2H_5)_4$), 11.1 parts by weight of an aqueous 20 wt % tetra-n-propylammonium hydroxide solution and 73 parts by weight of water were charged and stirred at room temperature for 24 hours, and then a hydrothermal synthesis reaction was carried out by stirring at 175° C. for 72 hours. The obtained slurry (reaction mixture) was filtered and the residue was continuously washed with ion exchanged water until the pH of the wash became around 7, and dried at 60° C.

The obtained dried product was calcined under nitrogen flow at 530° C. for 1 hour, and then calcined under air flow at 530° C. for 1 hour to obtain a powdery white crystal. This powdery white crystal was analyzed by powder X-ray diffraction. As a result, it was identified as a zeolite having a MFI structure.

Then, 1.6 g of the obtained powdery white crystal was charged in an autoclave and a treatment of adding a solution that is a mixture of an aqueous ammonium nitrate solution and an aqueous ammonia solution, and stirring and filtration was repeated three times in total in the same manner as in Example 1, and then washed with water and dried to obtain a pentasil type zeolite (C1) for comparison.

Production of ε-Caprolactam

In the same manner as in Example 1, except that a catalyst layer was formed by filling with 0.5 g of the pentasil type zeolite (C1) for comparison obtained above as a catalyst, a vapor phase Beckmann rearrangement reaction of cyclohexanone oxime was performed.

For 4 to 6 hours after the beginning of the reaction, the reaction gas was collected and, and then a conversion of cyclohexanone oxime and a selectivity of ε-caprolactam were determined in the same manner as in Example 1. As a result, the conversion of cyclohexanone oxime was 67.9% and the selectivity of ε-caprolactam was 87.5%.

Example 5

Production of Pentasil Type Zeolite (5)

Using a compound (II) represented by the general formula (II) in which $R^2$ is an n-propyl group, j is 5, B is an iodide ion and k is 1, namely, a compound ($dC_5.I^-$) represented by $[(C_3H_7)_3N^+—(CH_2)_5—N^+(C_3H_7)_3]·2I^-$, a pentasil type zeolite was produced.

In an autoclave made of stainless steel, 5.5 parts by weight of tetraethyl orthosilicate ($Si(OC_2H_5)_4$), 2.2 parts by weight of the compound (II) ($dC_5.I^-$), 0.7 part by weight of tetra-n-propylammonium iodide, 9.5 parts by weight of an aqueous 5.6 wt % potassium hydroxide solution and 82.1 parts by weight of water were charged and stirred at room temperature for 24 hours, and then a hydrothermal synthesis reaction was carried out by stirring at 150° C. for 168 hours. The obtained slurry (reaction mixture) was filtered and the residue was continuously washed with ion exchanged water until the pH of the wash became around 7, and dried at 60° C. to obtain a dried product. This dried product was analyzed by powder X-ray diffraction. As a result, it was identified as a zeolite having a MFI structure. This dried product was taken as a pentasil type zeolite (5).

Reference Example

Production of Pentasil Type Zeolite (6)

In an autoclave made of stainless steel, 5.5 parts by weight of tetraethyl orthosilicate ($Si(OC_2H_5)_4$), 2.9 parts by weight of the same compound (II) ($dC_5.I^-$) as in Example 5, 9.5 parts by weight of an aqueous 5.6 wt % potassium hydroxide solution and 82.1 parts by weight of water were charged and stirred at room temperature for 24 hours, and then a hydrothermal synthesis reaction was carried out by stirring at 150° C. for 168 hours. The obtained slurry (reaction mixture) was filtered and the residue was continuously washed with ion exchanged water until the pH of the wash became around 7, and dried at 60° C. to obtain a dried product. This dried product was analyzed by powder X-ray diffraction. As a result, it was identified as a zeolite having a MFI structure. This dried product was taken as a pentasil type zeolite (6).

What is claimed is:

1. A method for producing ε-caprolactam, which comprises performing a vapor phase Beckmann rearrangement reaction of cyclohexanone oxime in the presence of a pentasil type zeolite, wherein the pentasil type zeolite is a zeolite obtained by subjecting a mixture containing a silicon compound, water, and a compound represented by formula (I):

$$[(R^1)_3N^+—(CH_2)_m—N^+(R^1)_2—(CH_2)_m—N^+(R^1)_3]·3/n(A) \quad (I)$$

wherein $R^1$ represents an n-propyl group, A represents an iodide ion or hydroxide ion, m represents an integer of 6, and n represents an integer of 1, to a hydrothermal synthesis reaction.

2. The method for producing ε-caprolactam according to claim 1, wherein a mixture containing a silicon compound, water, a tetraalkyl ammonium salt, and a compound represented by the formula (I) is subjected to a hydrothermal synthesis reaction.

3. A method for producing ε-caprolactam, which comprises performing a vapor phase Beckmann rearrangement reaction of cyclohexanone oxime in the presence of a pentasil type zeolite, wherein the pentasil type zeolite is a zeolite obtained by subjecting a mixture containing a silicon compound, water, and a compound represented by formula (II):

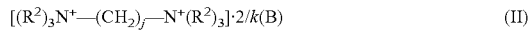
$$[(R^2)_3N^+-(CH_2)_j-N^+(R^2)_3] \cdot 2/k(B) \tag{II}$$

wherein $R^2$ represents an n-propyl group, B represents an iodide or a hydroxide ion, j represents an integer of 5, and k represents an integer of 1, to a hydrothermal synthesis reaction.

4. The method for producing ε-caprolactam according to claim 3, wherein a mixture containing a silicon compound, water, a tetraalkyl ammonium salt, and a compound represented by the formula (II) is subjected to a hydrothermal synthesis reaction.

* * * * *